(12) United States Patent  
Allred et al.

(10) Patent No.: US 7,874,674 B2
(45) Date of Patent: Jan. 25, 2011

(54) ABERROMETER HAVING REDUCED NOISE

(76) Inventors: Lloyd G. Allred, 132 Norton Village La., Rochester, NY (US) 14609; Barry T. Eagan, 945 Washington St., Spencerport, NY (US) 14559

( * ) Notice: Subject to any disclaimer, the term of this patent is extended or adjusted under 35 U.S.C. 154(b) by 486 days.

(21) Appl. No.: 11/955,003

(22) Filed: Dec. 12, 2007

(65) Prior Publication Data

US 2009/0153738 A1    Jun. 18, 2009

(51) Int. Cl.
*A61B 3/10*    (2006.01)
(52) U.S. Cl. ...................................... 351/221; 351/246
(58) Field of Classification Search ................. 351/205, 351/206, 221, 246
See application file for complete search history.

(56) References Cited

U.S. PATENT DOCUMENTS

| | | | |
|---|---|---|---|
| 4,582,863 A | 4/1986 | Wessling | |
| 4,925,610 A | 5/1990 | Wessling et al. | |
| 4,929,388 A | 5/1990 | Wessling | |
| 4,935,164 A | 6/1990 | Wessling et al. | |
| 5,069,820 A | 12/1991 | Jen et al. | |
| 5,160,456 A | 11/1992 | Lahn et al. | |
| 5,456,882 A | 10/1995 | Covain | |
| 5,476,612 A | 12/1995 | Wessling et al. | |
| 5,567,355 A | 10/1996 | Wessling et al. | |
| 5,720,903 A | 2/1998 | Wessling et al. | |
| 5,721,056 A | 2/1998 | Wessling | |
| 5,777,719 A | 7/1998 | Williams et al. | |
| 5,779,818 A | 7/1998 | Wessling | |
| 5,846,606 A | 12/1998 | Wessling | |
| 6,086,204 A | 7/2000 | Magnante | |
| 6,130,419 A | 10/2000 | Neal | |
| 6,199,986 B1 * | 3/2001 | Williams et al. | ............. 351/221 |
| 6,264,328 B1 | 7/2001 | Williams et al. | |
| 6,271,915 B1 | 8/2001 | Frey et al. | |
| 6,299,311 B1 | 10/2001 | Williams et al. | |
| 6,460,997 B1 | 10/2002 | Frey et al. | |
| 6,497,483 B2 | 12/2002 | Frey et al. | |
| 6,511,180 B2 | 1/2003 | Guirao et al. | |
| 6,565,209 B2 | 5/2003 | Campin | |
| 6,572,230 B2 | 6/2003 | Levine | |
| 6,575,572 B2 | 6/2003 | Lai et al. | |
| 6,595,642 B2 | 7/2003 | Wirth | |
| 6,609,794 B2 | 8/2003 | Levine | |
| 6,631,991 B2 | 10/2003 | Wirth | |
| 6,632,380 B1 | 10/2003 | Wessling | |
| 6,685,320 B2 | 2/2004 | Hirohara et al. | |
| 6,715,877 B2 | 4/2004 | Molebny | |

(Continued)

FOREIGN PATENT DOCUMENTS

JP    08-259709    10/1996

(Continued)

*Primary Examiner*—Huy K Mai
(74) *Attorney, Agent, or Firm*—Jeffrey B Powers

(57) ABSTRACT

Methods and apparatus for facilitating determination of centroids of image spots in an image containing an array of image spots generated by an aberrometer, the image comprising a first plurality of pixels each pixel having a corresponding intensity value, the method comprising calculating an average intensity value for a second plurality of pixels in a perimeter around a pixel, the average calculated using a subset of the second plurality exclusive of at least a portion of the pixels in the perimeter.

19 Claims, 5 Drawing Sheets

U.S. PATENT DOCUMENTS

| | | |
|---|---|---|
| 6,827,444 B2 | 12/2004 | Williams et al. |
| 6,948,818 B2 | 9/2005 | Williams et al. |
| 7,077,522 B2 | 7/2006 | Williams |
| 7,078,665 B2 | 7/2006 | Topa |
| 7,216,980 B2 | 5/2007 | Mihashi et al. |
| 7,249,851 B2 | 7/2007 | Hirohara et al. |
| 7,309,126 B2 | 12/2007 | Mihashi et al. |
| 7,335,867 B2 | 2/2008 | Topa |
| 2003/0086063 A1 | 5/2003 | Williams et al. |
| 2004/0021826 A1 | 2/2004 | Sarver et al. |
| 2006/0044510 A1 | 3/2006 | Williams et al. |
| 2006/0126018 A1 | 6/2006 | Liang |
| 2006/0126019 A1 | 6/2006 | Liang et al. |
| 2006/0203198 A1 | 9/2006 | Liang |

FOREIGN PATENT DOCUMENTS

| | | |
|---|---|---|
| WO | WO 03/020167 A2 | 3/2003 |
| WO | WO 2005/015290 A2 | 2/2005 |

\* cited by examiner

ABERROMETER HAVING REDUCED NOISE

FIELD OF INVENTION

The present invention relates to aberrometers, and more particularly to noise reduction in aberrometer images.

BACKGROUND OF THE INVENTION

Accurate characterization of wavefronts produced by an eye is desirable in the field of ophthalmology to facilitate correction of an eye's image-forming system through surgery and/or corrective lens fabrication.

Although various types of aberration measurement apparatus (hereinafter, "aberrometers") are known, Hartmann-Shack type aberrometers are widely used in commercial ophthalmic applications. FIG. 1 is a simplified schematic illustration of an example of a Hartmann Shack aberrometer 100.

In use, a beam of light from a light source 110 in the aberrometer is directed toward the cornea C of an eye E and onto the retina R by beam splitter 120. The light reflects from the retina and is projected through the cornea, and forms an aberrated wavefront. The aberrated wavefront reenters the aberrometer, and is incident on an array of lenslets 130. The light forms an array spots $d_{11}$-$d_{1n}$ on sensor 140. The locations of the spots relative to the locations that spots would have occupied in the absence of wavefront aberrations provides data that is used to characterize the wavefront and thus detect aberrations. FIG. 2 is a graphical illustration of example intensity values on a representative area of sensor 140 (including a plurality of spots $d_{i,j}$).

A seminal reference in the field of ophthalmic wavefront detection is Liang et al., *Objective measurement of wave aberrations of the human eye with the use of a Hartmann-Shack wave-front sensor*, Journal of the Optical Society of America, Vol. 11, No. 7, pp. 1-9 (July 1994), the disclosure of which is hereby incorporated by reference in its entirety. Improvements to the technique of Liang et al., id., are taught in Liang and Williams, *Aberrations and retinal image quality of the normal human eye*, Journal of the Optical Society of America, Vol. 4, No. 11, pp. 2873-2883 (November 1997), and in Williams et al. U.S. Pat. No. 5,777,719, the disclosures of which are hereby incorporated by reference in their entireties.

The ability to accurately measure aberrations and use the measurement information in corrective applications depends on the ability to precisely determine the location of the centers of the spots associated with each lenslet in an array. An inability to accurately detect the centers of all image spots frustrates the characterization of the wave aberrations and subsequent procedures that rely upon those characterizations.

Typically, center coordinates $c_x$, $c_y$ of an image spot are calculated by centroid calculation (i.e., summation of weighted values of the incident light intensity $I(x_i, y_i)$ at points $(x_i, y_i)$ on sensor 140). Many known factors operate to frustrate accurate centroid determination. For example, scattered light (i.e., noise) from the aberrometer componentry or from the eye itself can form ghost images and/or create background light on the detector that interferes with actual image spot detection and subsequent centroid determination. Image processing techniques that employ high band-pass filtering or certain linear filters may provide a reduced noise component; however, such filtering may also create significant edge distortion and/or may alter the size and shape of a feature of the image (e.g., due to aliasing or ringing).

SUMMARY

Aspects of the present invention are directed to removal of background noise and/or ghost images while avoiding or limiting distortion of spot images in an aberrometer image.

An aspect of the invention is directed to a method for facilitating determination of centroids of image spots in an image containing an array of image spots generated by an aberrometer, the image comprising a first plurality of pixels each pixel having a corresponding intensity value. The method comprises calculating an average intensity value for a second plurality of pixels in a perimeter around a first pixel, the average calculated using a subset of the second plurality exclusive of at least a plurality of the pixels in the perimeter.

In some embodiments, the method comprises subtracting the average value from the intensity value of the first pixel.

In some embodiments, the step of calculating is repeated for each of the first plurality of pixels. In other embodiments, the step of calculating is repeated for only a second subset of the first plurality of pixels whereby each of the pixels in the second subset is assigned a corresponding average intensity value.

In some embodiments, the method comprises subtracting the average value assigned to each pixel in the second subset from the intensity value of a corresponding pixel in the image. The method may further comprise calculating a centroid corresponding to each of the image spots.

In some embodiments, the pixels in the subset of the second plurality of pixels are selected as those pixels having intensity values less than a selected maximum intensity value. In some embodiments, the pixels in the subset of the second plurality of pixels are selected by omitting a predetermined number of pixels having the highest intensity values of the second plurality of pixels. In some embodiments, both techniques of selection are used.

In some embodiments, the second subset of the first plurality of pixels is selected as every $n^{th}$ pixels, where n>2. In some embodiments, the step of assigning an intensity value of a pixel in the second subset to a pixel that is not in the second subset.

Another aspect of the invention is directed to an aberrometer comprising a light source configured and arranged to project light onto a subject's eye, a lenslet array configured and arranged to receive the light after it reflected form a retina of the eye, a sensor adapted to receive an image containing an array of image spots from lenslet array, the sensor comprising a first plurality of pixels each pixel having a corresponding intensity value, and a processor coupled to the sensor adapted to calculate an average intensity value for a second plurality of pixels in a perimeter around a first pixel of said first plurality of pixels, the average calculated using a subset of the second plurality exclusive of at least a plurality of the pixels in the perimeter.

Another aspect of the invention is directed to a method for facilitating determination of centroids of image spots in an image containing an array of image spots generated by an aberrometer, the image comprising a first plurality of pixels each pixel having a corresponding intensity value, the method comprising 1) identifying a perimeter about a selected (at least one) pixel, the perimeter including a second plurality of pixels, 2) calculating an average intensity value, using a subset of the second plurality of pixels; and 3) assigning the average value to the selected pixel.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Aspects of the present invention are directed towards a method for facilitating determination of centroids of image spots in an image containing an array of image spots generated by an aberrometer. The image comprises a first plurality of pixels as determined by a sensor, each pixel having a corresponding intensity value. The method comprises calculating an average intensity value for a second plurality of pixels in a perimeter around a pixel. According to aspects of the present invention, the average is calculated using a subset of the second plurality exclusive of at least a portion (e.g., a plurality) of the pixels in the perimeter. To form the subset, pixels including selected or substantial amounts of non-scattered lights (i.e., light directly projected in the spots) are omitted.

Figure 1:
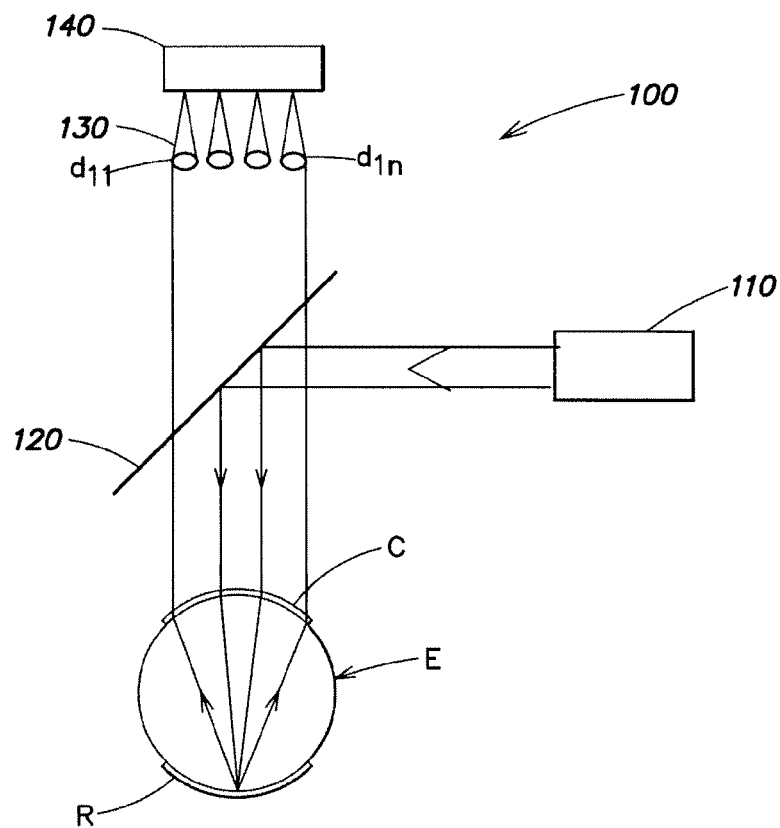
FIG. 1 is a simplified schematic illustration of a Hartmann Shack aberrometer projecting light onto an eye and producing a plurality of spots on a sensor.
Figure 3:
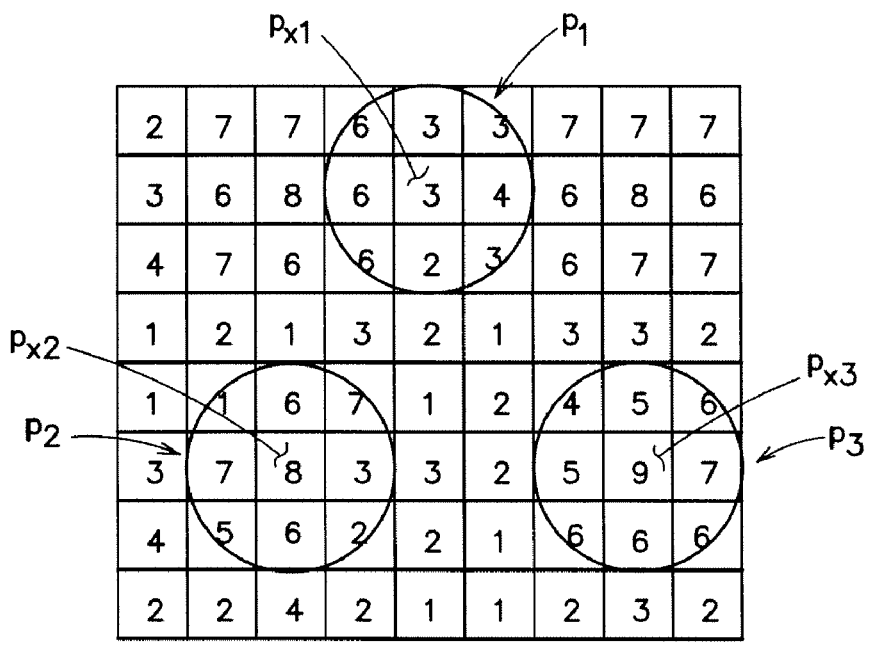
FIG. 3 is a numerical representation of intensity values for a representative area of the sensor in the aberrometer shown in FIG. 1.

Examples of embodiments of methods and apparatus suitable for performing aspects of the present invention will now be discussed with reference to FIGS. 3-7. The graphical data is provided to facilitate discussion and is not drawn to scale. FIG. 3 is a numerical representation of intensity values for pixels in a representative area of a sensor (e.g., sensor 140 shown in FIG. 1) when an image is projected thereon. As stated above, the image contains an array of image spots generated by an aberrometer. The image on the sensor comprises a first plurality of pixels on which the plurality of spots is projected, each pixel having a corresponding intensity value. The intensity values are, for example, gray scale values of a digitization of the image. For example, the gray scale may range from 0-255.

It will be appreciated that the image spots correspond with peaks in the intensity values in the image; however, noise may obscure the peaks corresponding to the image spots. Aspects of the present invention are directed to removal of noise from an image to facilitate spot location determination. In particular, aspects of the present invention facilitate using centroiding techniques to determine spot location.

In accordance with aspects of the invention, FIG. 3 illustrates perimeters $p_1$, $p_2$, $p_3$ identified about selected pixels $px_1$, $px_2$, $px_3$ in the image according to aspects of the present invention. Each perimeter includes a corresponding second plurality of pixels. In some embodiments, the span (e.g., diameter) of the perimeter is selected to be equal to the pitch (e.g., the number of pixel) between spots in the image as determined to be equal to the pitch of lenslet 130 (shown in FIG. 1). However, a perimeter having such a size is not necessary. The perimeter is typically equal to or less than the spot pitch and is selected to include a substantial number of pixels that are remote from the location in which a spot is located so as to include pixels that contain substantially only noise.

It will be understood that, although the perimeter in the illustrated embodiment is circular, a perimeter having any suitable shape (e.g., polygonal) may be used. Typically the perimeter about a selected pixel will be symmetric about that selected pixel; however, in some embodiments the perimeter may be asymmetric about the pixel.

Figure 4:
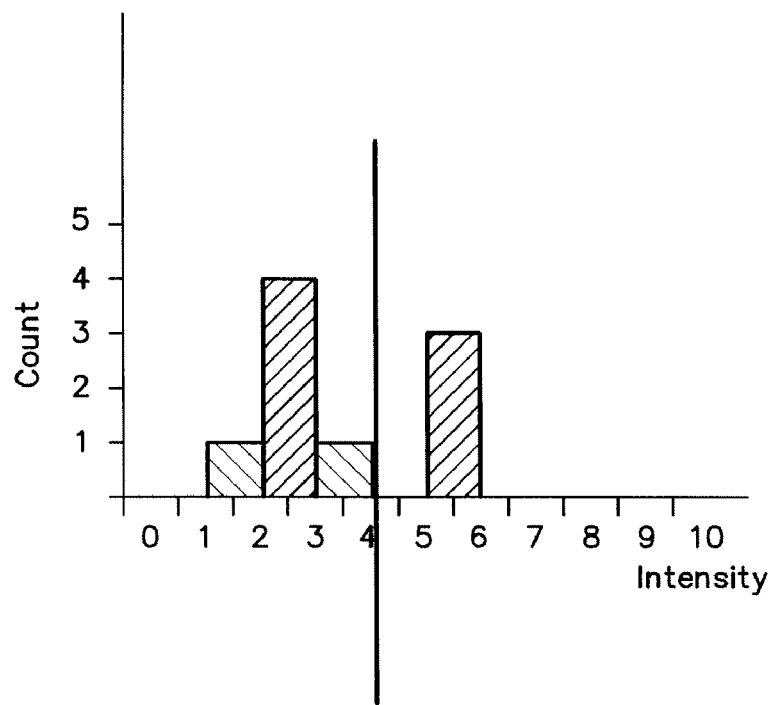
FIG. 4 is a histogram of intensity values within a perimeter about a representative point in a representative area of FIG. 3.

In accordance with aspects of the invention, FIG. 4 illustrates a frequency distribution of the intensity values for the second plurality of pixels. A histogram is shown for the sake ease of description; any suitable technique for determining an average intensity value as described below may be used. FIG. 4 illustrates a histogram of intensity values for a representative selected pixel $px_1$ in the representative area image output of FIG. 3. Using the pixels in the perimeter, an average intensity value is calculated for the pixel $px_1$. In some embodiments, pixels through which the perimeter extends may be included in the perimeter.

A subset of the second plurality of pixels is selected to characterize the noise in the image. According to aspects of the present invention, prior to making calculations characterizing the noise in an image, pixels including substantial amounts of non-scattered lights from spots are eliminated to facilitate noise characterization. For example, determining which pixel to eliminate can be achieved by determining a threshold intensity value with pixels having an intensity greater than the threshold being assumed to be associated with a spot and therefore eliminated from the subset. Alternatively, pixels having a substantial amount of non-scattered light can be eliminated from the subset assuming that a selected percentage (or a selected number) of the pixels (in the perimeter) having relatively high intensity values are associated with spots (e.g., 15%).

In summary, pixels to be used to calculate an average can be selected by 1) including, in the subset, pixels of the second plurality having an intensity value less than a selected intensity value or 2) including, in the subset, a selected percentage of pixels of the second plurality having the lowest intensities (e.g., 85% of the pixels in the second plurality are included). In some embodiments, pixel selection can be achieved by using two or more selection techniques. For example, a selected percentage of pixels in the second plurality (e.g., 15%) can be eliminated; subsequently, if a portion of the remaining pixels having intensities greater than a selected threshold intensity, the pixels in the portion are eliminated from the subset.

Figure 5:
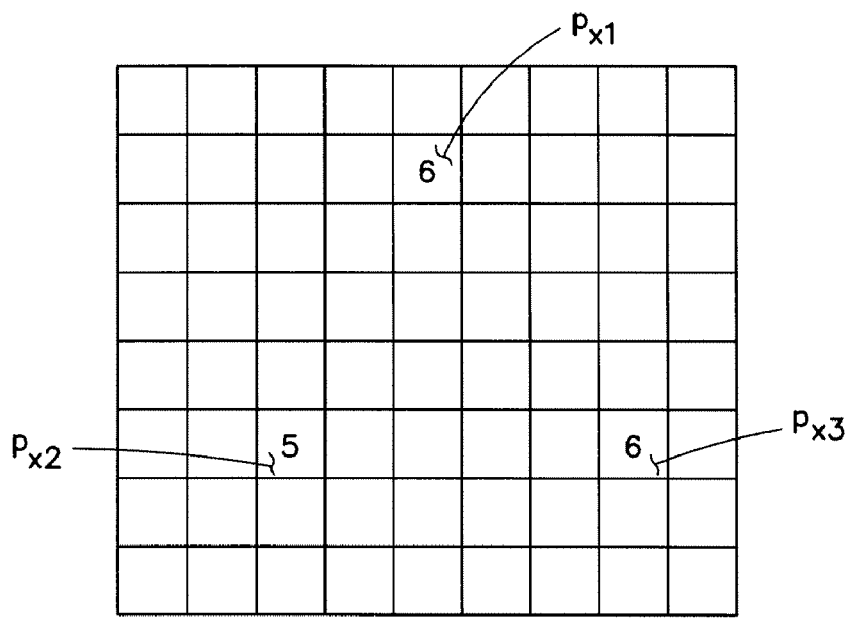
FIG. 5 is a numerical representation of intensity values for a noise component of selected pixels in the representative area shown in FIG. 3 calculated according to aspects of the present invention.

An average intensity value is calculated using the pixels in the subset. After calculation, the average intensity value is assigned to the selected pixel as shown in FIG. 5. The steps of assigning values are performed for the remainder of the image. However, the total number of pixels for which an average value is calculated using the elimination and averaging steps as set forth above may be less than all of the pixels in the image (i.e., an average intensity value is calculated for 1 in every n pixels in a given direction, where n>2). In some embodiments, the pixels for which an average value is calculated are distributed throughout the image. For example, for an image sensor having a rectilinear grid of pixels, every fifth pixel in the vertical direction and every fifth pixel in the horizontal direction may be used.

In the event that less than all of the pixels have calculated values as set forth above, an estimated value can be assigned to pixels not having a calculated value. The estimated value may be generated by assigning an intensity value of a proximately-located pixel having a calculated value (e.g., each pixel not having a calculated value receives the value of its closest neighbor having a calculated value).

It will be appreciated that a decision to perform the calculation steps on only a subset of pixels is a tradeoff between speed of calculation and accuracy of the noise analysis. Generally, the less spatially-dependent the noise content is, the more spaced the pixels on which calculation are performed may be. The number of pixels and the locations of the pixels will depend on the configuration of a given aberrometer.

After all pixels have been assigned an average value, the noise component has been characterized (e.g., quantified). It will be appreciated that FIG. 5 is a numerical representation of intensity values for a noise component of selected pixels in the representative area image output shown in FIG. 3. Averages for only pixels $px_1$, $px_2$, $px_3$ are shown; however, other pixels in the area can be assigned calculated or approximate noise values as forth above.

Figure 2:
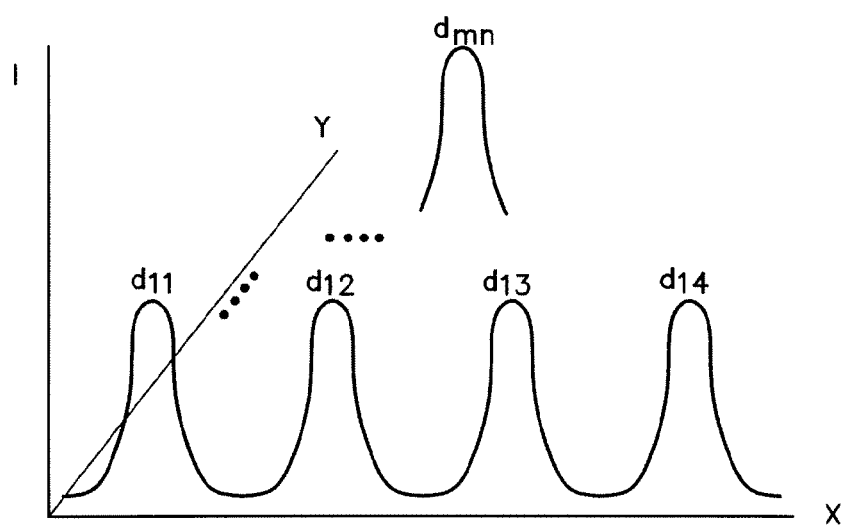
FIG. 2 is a graphical illustration of example intensity values on a representative area of the sensor in the aberrometer shown in FIG. 1.
Figure 6:
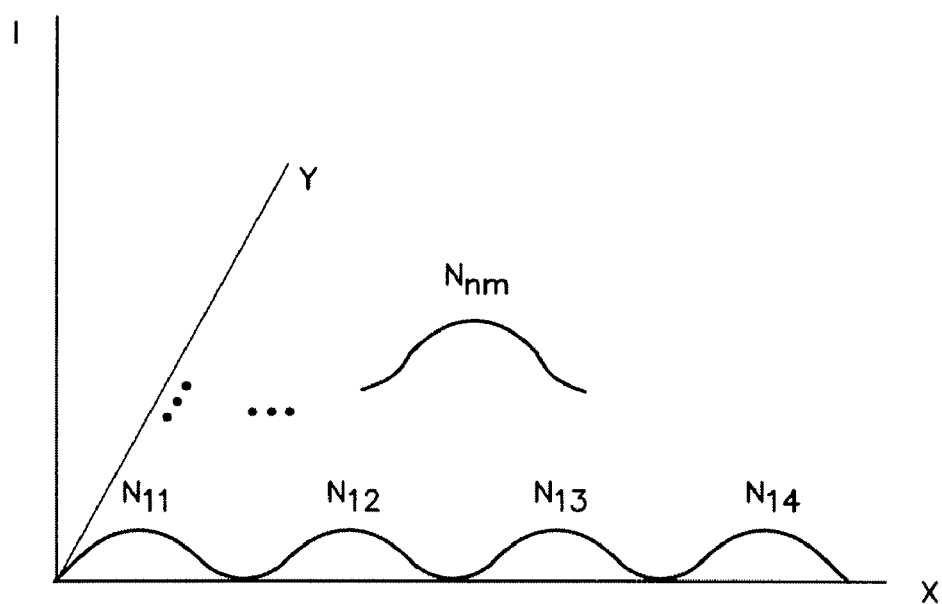
FIG. 6 is a graphical illustration of intensity values for a noise component of the representative area shown in FIG. 2.

FIG. 6 is a graphical illustration of intensity values for a noise component of the representative area image output shown in FIG. 2. As shown, typically, the noise component is more uniform in intensity than the original image; however, the noise component is somewhat larger for pixels nearer to spots. The increase in noise nearer to spots is expected since the light scatter nearer the spots will be of greater intensity.

After a noise value is assigned to each pixel, a value corresponding to the noise component is subtracted from value in the original image, on a pixel by pixel basis.

$$S_{m,n} = D_{m,n} - N_{m,n}$$

Figure 7:
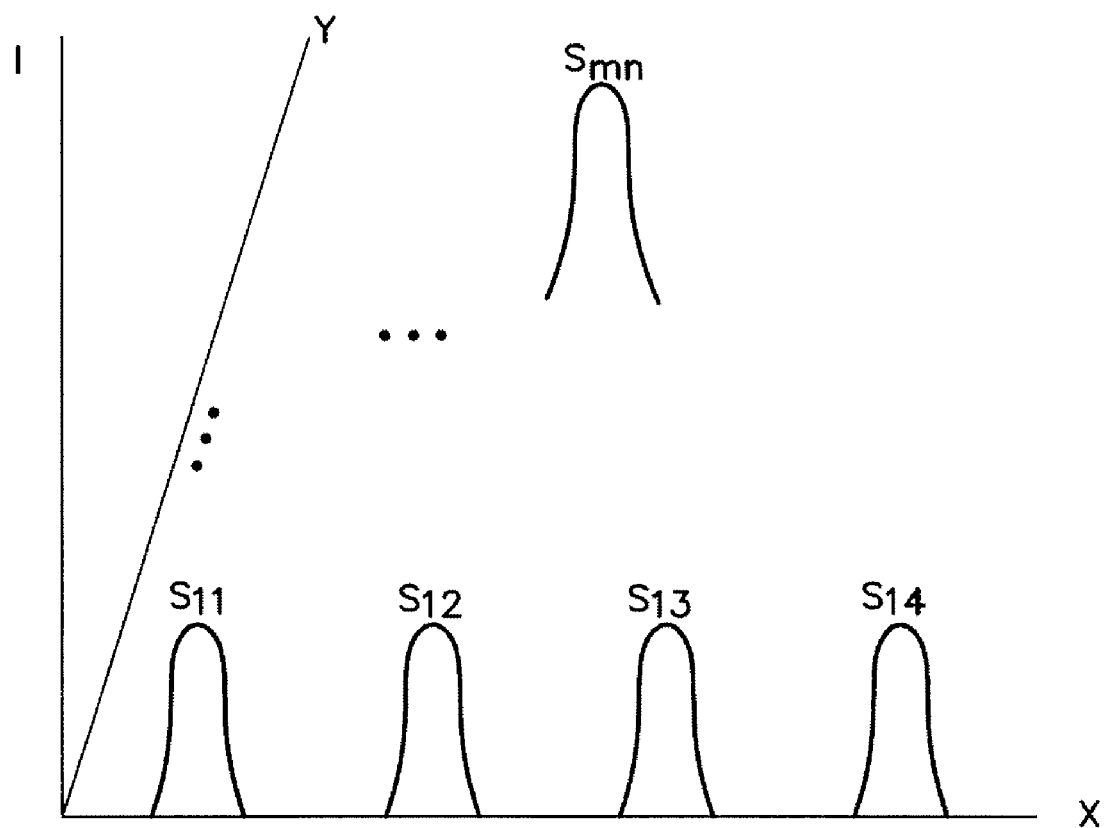
FIG. 7 is a graphical illustration of intensity values of FIG. 2 after subtraction of background noise calculated according to aspects of the present invention.

FIG. 7 is a graphical illustration of intensity values of FIG. 2 after subtraction of background noise. As shown, typically, the peaks associated with spots become more identifiable, and subsequent centroid calculation become more accurate. After subtraction of the noise, any suitable known or yet to be developed technique to identify spots and to calculate the centroids of the spots may be used.

Figure 8:
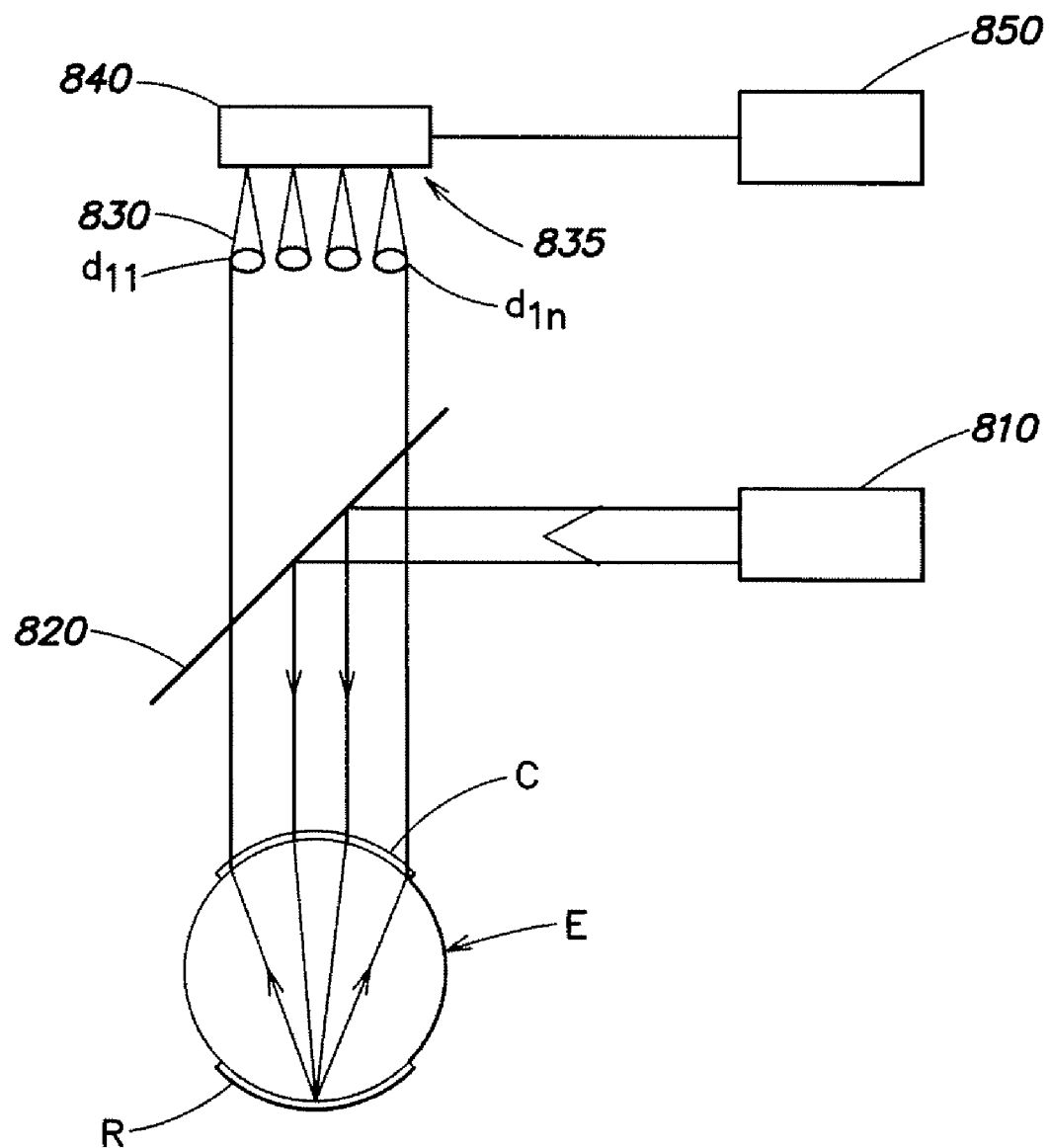
FIG. 8 is a simplified schematic illustration of a Hartmann Shack aberrometer projecting light onto an eye and producing a plurality of spots on a sensor according to aspects of the present invention.

FIG. 8 is a simplified schematic illustration of an example of a Hartmann Shack aberrometer 800 according to aspects of the present invention. In a conventional manner, a beam of light from a light source 810 in the aberrometer is directed toward the cornea C of an eye E and onto the retina R by beam splitter 820. A chin rest or forehead rest or other suitable positioning apparatus (not shown) may be provided to move or maintain an eye in a suitable position such that the beam is incident on the retina.

Light reflects from the retina and is projected through the cornea, and forms an aberrated wavefront. The aberrated wavefront reenters the aberrometer, and is incident on an array of lenslets 830. The light forms an image containing an array spots 835 on sensor 840. The sensor is configured such that the image comprises a first plurality of pixels, each pixel having a corresponding intensity value.

A processor 850 is coupled to the sensor in a manner to receive pixel intensity data from the sensor. The processor is programmed to facilitate determination of centroids of image spots in the image by calculating an average intensity value for a second plurality of pixels in a perimeter around a pixel, the average calculated using a subset of the second plurality exclusive of at least a portion of the pixels in the perimeter, as set forth above. Subsequently, after pixels are assigned a noise value, the processor may subtract the noise value from the intensity value in the image, spots may be identified, and centroids may be calculated using any suitable known or yet to be developed techniques.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A method for facilitating determination of centroids of image spots in an image containing an array of image spots generated by an aberrometer, the image comprising a first plurality of pixels each pixel having a corresponding intensity value, the method comprising:

calculating an average intensity value for a second plurality of pixels in a perimeter around a first pixel, the average calculated using a subset of the second plurality exclusive of at least a plurality of the pixels in the perimeter; and subtracting the average value from the intensity value of the first pixel.

2. The method of claim 1, wherein the step of calculating is repeated for each of the first plurality of pixels.

3. The method of claim 1, wherein the step of calculating is repeated for only a second subset of the first plurality of pixels whereby each of the pixels in the second subset is assigned a corresponding average intensity value.

4. The method of claim 3, further comprising subtracting the average value assigned to each pixel in the second subset from the intensity value of a corresponding pixel in the image.

5. The method of claim 4, further comprising calculating a centroid corresponding to each of the image spots.

6. The method of claim 3, wherein the second subset of the first plurality of pixels is selected as every $n^{th}$ pixels, where n >2.

7. The method of claim 3, further comprising a step of assigning an intensity value of a pixel in the second subset to a pixel that is not in the second subset.

8. The method of claim 1, wherein the pixels in the subset of the second plurality of pixels are selected as those pixels having intensity values less than a selected maximum intensity value.

9. The method of claim 1, wherein the pixels in the subset of the second plurality of pixels are selected by omitting a predetermined number of pixels having the highest intensity values of the second plurality of pixels.

10. An aberrometer comprising:
    a light source configured and arranged to project light onto a subject's eye;
    a lenslet array configured and arranged to receive the light after it reflected form a retina of the eye;

a sensor adapted to receive an image containing an array of image spots from lenslet array, the sensor comprising a first plurality of pixels each pixel having a corresponding intensity value;

a processor coupled to the sensor adapted to calculate an average intensity value for a second plurality of pixels in a perimeter around a first pixel of said first plurality of pixels, the average calculated using a subset of the second plurality exclusive of at least a plurality of the pixels in the perimeter, wherein the processor is further adapted to subtract the average value from the intensity value of the first pixel.

11. The aberrometer of claim 10, wherein a span of the perimeter is substantially equal to a pitch between the spots.

12. The aberrometer of claim 10, wherein the processor is adapted to calculate an average value for each of the first plurality of pixels.

13. The aberrometer of claim 10, wherein the processor is adapted to calculate an average value for only a second subset of the first plurality of pixels.

14. The aberrometer of claim 13, wherein the processor is further adapted to subtract the average value assigned to each pixel in the second subset from the intensity value of a corresponding pixel in the image.

15. The aberrometer of claim 14, wherein the processor is further adapted to calculate a centroid corresponding to each of the image spots.

16. The aberrometer of claim 13, wherein the processor is programmed such that the second subset of the first plurality of pixels is selected as every $n^{th}$ pixels, where n>2.

17. The aberrometer of claim 13, wherein the processor is programmed to assign an intensity value of a pixel in the second subset to a pixel that is not in the second subset.

18. The aberrometer of claim 10, wherein the processor is programmed such that the pixels in the subset of the second plurality of pixels are selected as those pixels having intensity values less than a selected maximum intensity value.

19. The aberrometer of claim 10, wherein the processor is programmed such that the pixels in the subset of the second plurality of pixels are selected by omitting a predetermined number of pixels having the highest intensity values of the second plurality of pixels.

* * * * *